US00PP34304P2

(12) United States Plant Patent
Hansen

(10) Patent No.: US PP34,304 P2
(45) Date of Patent: Jun. 7, 2022

(54) ***PEROVSKIA* PLANT NAMED 'PRIME TIME'**

(50) Latin Name: ***Perovskia atriplicifolia* (Benth.)**
Varietal Denomination: Prime Time

(71) Applicant: Hans A Hansen, Zeeland, MI (US)

(72) Inventor: Hans A Hansen, Zeeland, MI (US)

(73) Assignee: Walters Garden, Inc., Zeeland, MI (US)

( * ) Notice: Subject to any disclaimer, the term of this patent is extended or adjusted under 35 U.S.C. 154(b) by 0 days.

(21) Appl. No.: 17/803,079

(22) Filed: Feb. 1, 2022

(51) Int. Cl.
*A01H 6/50* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para

(57) ABSTRACT

The new and distinct cultivar of ornamental, hardy, Russian Sage plant, *Perovskia* 'Prime Time' with medium height, dense habit of strong erect stems that remain upright through the growing season. The new plant is vigorous with many large, densely-arranged, rich lavender-purple flowers on branched stems with dark purplish-red calyces. Foliage is grey-green, simple, rhombic, fragrant and is retained well throughout the growing season.

2 Drawing Sheets

Botanical classification: *Perovskia atriplicifolia* (Benth.).
Variety denomination: 'Prime Time'.

STATEMENT REGARDING PRIOR DISCLOSURES UNDER 37 CFR 1.77(B)(6)

The claimed plant was first sold privately to Plantipp in the Netherlands on Mar. 1, 2021 by Walters Gardens, Inc., who obtained the plant and all information relating thereto, from the inventor. No plants of *Perovskia* 'Prime Time' have been sold to the public in this country or anywhere in the world, nor has any disclosure of the new plant been made, more than one year prior to the filing date of this application, and such sale or disclosure within one year was either derived directly or indirectly from the inventor and would be considered a 35 U.S.C. 102(b) exception.

BACKGROUND OF THE INVENTION

The present invention relates to a new and distinct plant of Russian sage, botanically known as *Perovskia* 'Prime Time' and will be referred to hereinafter also by its cultivar name 'Prime Time' and the new plant. The new plant cultivar of *Perovskia* is a winter-hardy semi-woody perennial useful for landscaping purposes.

'Prime Time' was hybridized by the inventor at a wholesale perennial nursery in Zeeland, Mich. in late July 2017 between an unintroduced siblings known only by their hybrid code numbers, 14-1-1 (not patented) as the female and 'Sage Advice' U.S. Plant Pat. No. 33,310 as the male. The seed was collected in October of 2017 and sown in spring of 2018 at the same nursery in Zeeland, Mich. The new plant was a single plant selected from among many seedlings and given the breeder code 18-3-6 during the evaluation process. *Perovskia* 'Prime Time' was originally selected in the summer of 2020. All subsequent evaluations were performed in a full-sun trial garden at the same nursery with loamy sand soil and irrigation and fertilizer as required. The plant was propagated by stem cuttings at the same nursery in Zeeland, Mich. in 2019 and the original plant and the cuttings evaluated over the next two years until final approval for introduction in the summer of 2019. The resultant asexually propagated cuttings have been stable and identical to the original plant in successive asexual propagations.

SUMMARY OF THE INVENTION

*Perovskia* 'Prime Time' differs from its parent as well as all other hardy Russian sage known to the inventor in a combination of traits. The following characteristics in combination distinguish 'Prime Time' from all other *Perovskia* plants known to the inventor:

1. Medium height, dense habit with strong, erect, dense stems that remain upright through the growing season;
2. Long flowering season of large, densely-arranged, rich lavender-purple flowers on branched stems;
3. Effective flowering time extended with dark purplish-red calyxes;
4. Earlier flowering time;
5. The foliage is grey-green, simple, rhombic and fragrant;
6. Vigorous growth rate.

The nearest comparison plants known to the inventor are the parent plant *Perovskia* 'LISSLITT' U.S. Plant Pat. No. 20,845, 'Denim 'n Lace' U.S. Plant Pat. No. 28,445, 'Rocketman' U.S. Plant Pat. No. 27,526 and 'Blue Jean Baby' U.S. Plant Pat. No. 29,281 and 'Sage Advice' U.S. Plant Pat. No. 33,310.

'LISSLITT' is slightly shorter and more open habit with less upright stems and more open that are more prone to lodging, and the inflorescence is branched in a wider angle. 'Denim 'n Lace' has smaller habit in height and width, the foliage is more finely doubly-cleft and the flowers begin earlier in the season and are not as deep lavender-purple. 'Rocketman' has a habit that is shorter and more open. 'Blue Jean Baby' has a shorter habit, flowers that are more lavender-blue and less lavender-purple, the flowering season begins slightly earlier, and foliage is more doubly-cleft. The new plant flowers approximately one week earlier than all of the above comparison varieties.

The female parent has more silver foliage, a more open mounding habit and more dissected foliage and the male parent, 'Sage Advice' differs by having a smaller habit more mounded habit. Both the female and male both flower about a week later than the new plant.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a three-year-old plant grown in full sun field in loamy sand soil in trial gardens of a nursery in Zeeland, Mich.

DETAILED BOTANICAL DESCRIPTION

Figure 1:
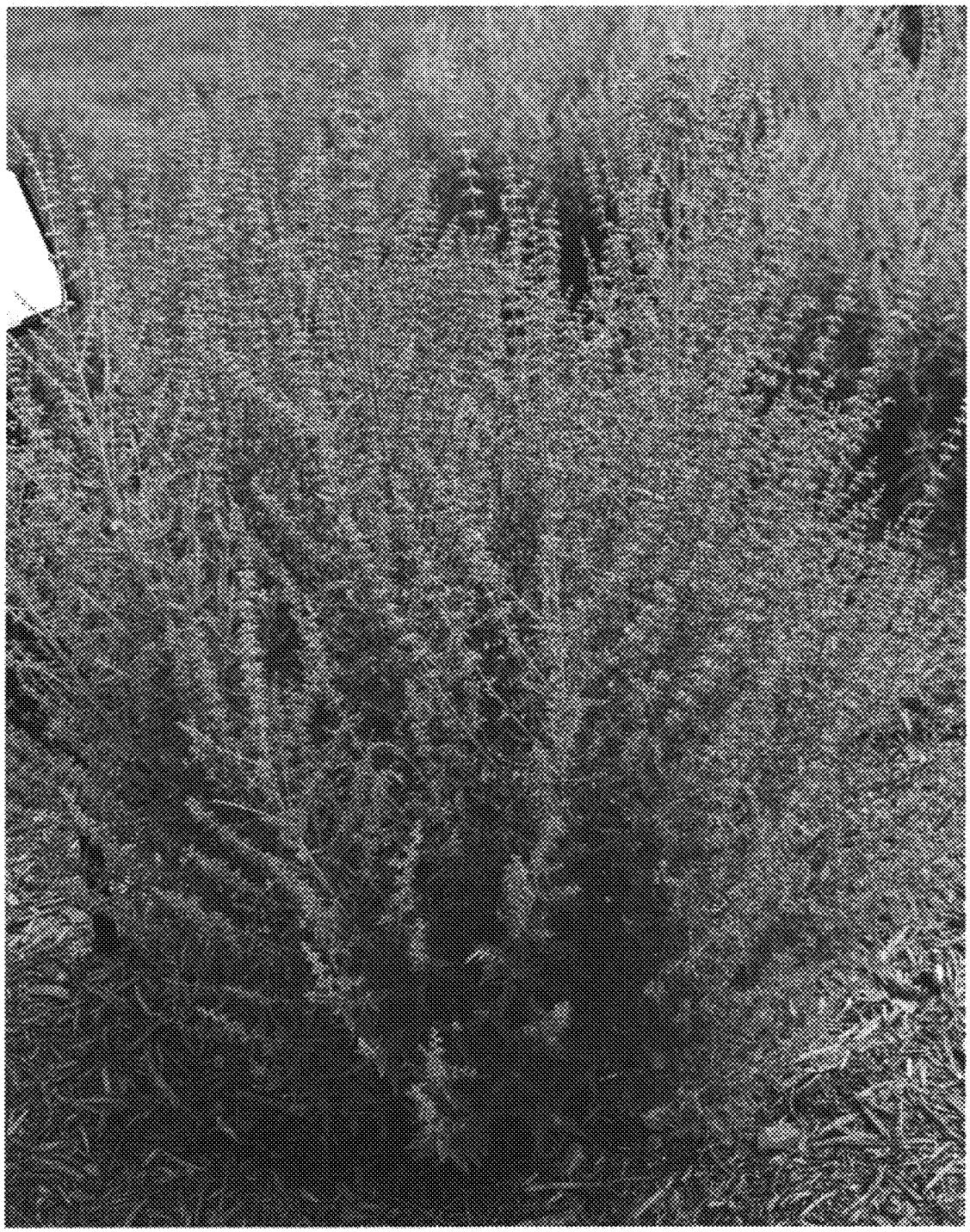
FIG. 1 shows the flowering habit of the new plant.
Figure 2:
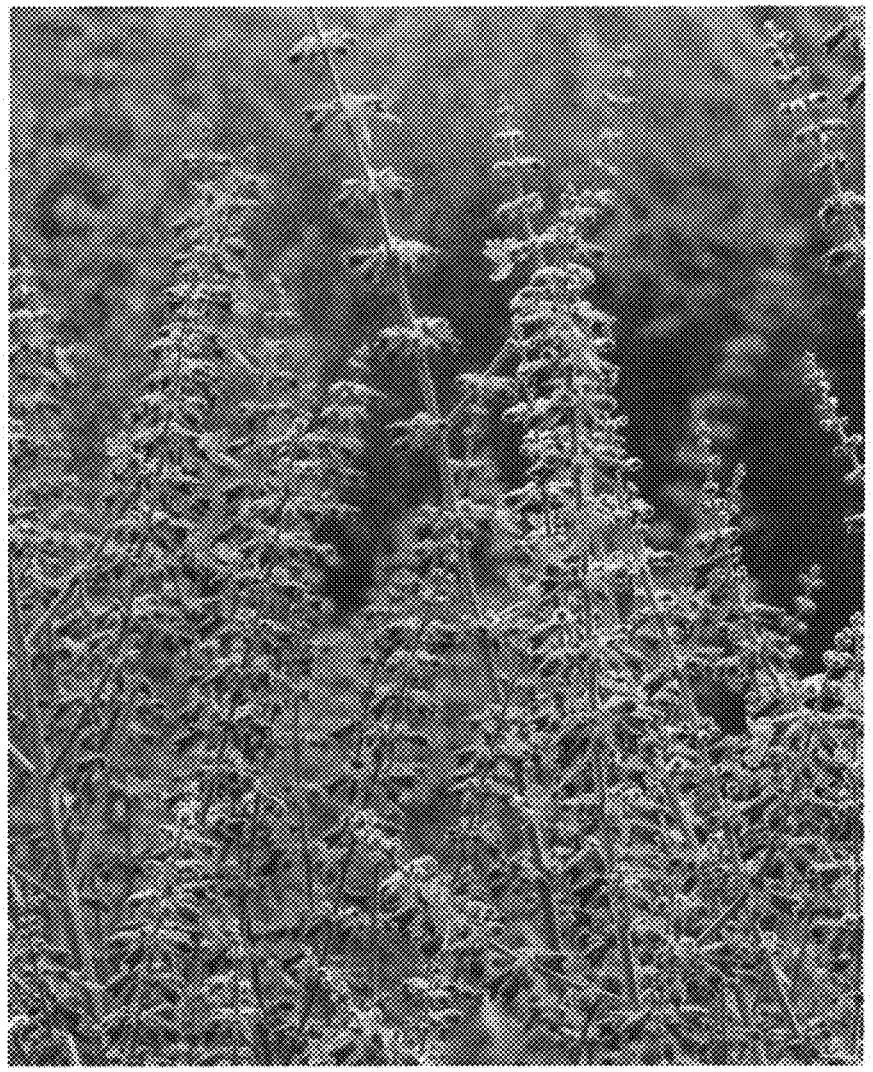
FIG. 2 shows a close-up of the flower sterns of the new plant.

The following is a detailed description of *Perovskia* 'Prime Time' as observed and compared to other cultivars for three years in trial gardens and production fields at a nursery in Zeeland, Mich. The following description is of a three-year-old plant of *Perovskia* 'Prime Time' in a full-sun trial garden in Zeeland, Mich. with limited irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2015 edition of The R.H.S. Colour Chart of The Royal Horticultural Society, London, England, except where common dictionary color terms are used.

Plant habit: Upright and dense mound; heavily oppositely branched; deciduous, semi-woody sub-shrub usually dying to the ground in most Michigan winters and re-sprouting with new stems from the base each spring; about 38 stems per plant;

Plant size: To about 110 cm in height and about 115 cm in width at the widest point about 30 cm above soil;

Root description: Fibrous; color nearest RHS 155D;

Propagation: Stem cuttings; root initiation occurs in about 14 days at a temperature of 20° C.;

Growth rate: Vigorous;

Crop time: About 10 to 14 weeks to produce flowering plant from rooted plug;

Stem description: Quadrangular; oppositely branched; young portions farinose; older stems becoming woody at base; average about 102 cm long and about 16 mm across near base; about 18 branches per stem; with herbal fragrance;

Stem color: Nearest RHS 189D;

Internode length: Average 2.5 cm;

Internode color: Same as surrounding stem;

Branches: Quadrangular; opposite; farinose; held about 45° angle above horizontal; lower branches about 18 cm long and about 1.2 mm diameter at base, decreasing distally to upper branches about 6 cm long and about 1 mm diameter;

Branch color: Nearest RHS 189D;

Foliage description: Opposite; rhombic; simple; acute apex; cuneate base; margin irregularly crenate; micro-farinose on abaxial and adaxial surface; with herbal fragrance;

Leaf size: To about 37 mm long and about 19 mm wide near middle, shorter in distal region, average about 35 mm long and about 16 mm wide;

Leaf color: Young adaxial nearest RHS 191B, abaxial nearest RHS 191B; mature adaxial nearest RHS N138B and abaxial between RHS N138B and RHS N138C;

Leaf venation: Pinnate; farinose adaxial and costate and farinose abaxial;

Vein color: Young adaxial nearest RHS 188C and abaxial nearest RHS 190B; mature adaxial midrib and secondary veins nearest RHS 194A; abaxial midrib between RHS 148C and RHS 148D with secondary veins nearest RHS 147C;

Petiole: Slightly concavo-convex, glabrous; sessile to about 6 mm long and about 1 mm across, average about 4.5 mm long and about 1 mm across at base;

Petiole color: Adaxial nearest RHS 189A; abaxial between RHS 193A and RHS 194B;

Peduncle: Main stems vertical, branched verticillate panicle; about 10 cm tall above last branch and flowering to about 36 cm long and 18 cm wide and about 2 cm across above last branch;

Peduncle color: Nearest RHS 189D;

Pedicel: Cylindrical; pubescent; curved slightly downward; about 1 mm long and 0.5 mm diameter;

Pedicel color: Variable depending on light exposure, high light nearest RHS N77D and low light nearest RHS 138A;

Flower buds about one day prior to opening: Terete to oblong; rounded apex; rounded base; abaxial calyx with dense pubescence about 1.0 mm long; about 6 mm long and about 2 mm diameter near apex;

Bud color: Abaxial calyx hairs nearest RHS N81C; calyx between RHS 138B and RHS 138C with strong blush on dorsal side nearest RHS 83A; extended unopened petal between RHS 93B and RHS N89D;

Flowers: Perfect; complete; zygomorphic; borne in verticils; bilabiate with upper and lower lip fused in about basal 6.5 mm; about 13 mm long to exserted style, about 9 mm tall and about 8 mm across; face opening to nearly flat;

Inflorescence: Flowering in distal 36 cm and 18 cm wide; side branches with up to 14 verticils, up to 20 flowers per verticil, up to 210 flowers per branch, main center stem with up to 70 flowers per verticil and 600 flowers total up to 2000 flowers per total inflorescence stem;

Flower attitude: Outwardly to slightly drooping;

Fragrance: Slight herbal;

Corolla: Bilabiate; 11 mm long and 6 mm wide fused in basal 6.5 mm; upper and lower lips meet in about an 80-degree angle; adaxial and abaxial glabrous except adaxial center about 2 to 4 mm from base pubescent;

*Upper lip*.—Four-lobed, puberulent adaxial center; glabrous abaxial; outer two lobes obtuse to ovate, 2 mm long and 2.5 mm wide at fusion, rounded apex, entire margin; inner two lobes rounded with rounded apex, 1.5 mm long and 2 mm wide.

*Lower lip*.—Single lobe, nearly flat with rounded apex and entire margin; about 6.5 mm long and about 1.0 mm wide at fusion point; basal 6.5 mm fused into tube; tube about 2.5 mm in width; glabrous abaxial, adaxial throat puberulent.

Corolla color: Adaxial nearest RHS 93B with veins of nearest RHS 83A and adaxial base nearest RHS NN155D; abaxial nearest RHS 92 and base nearest RHS NN155D;

Gynoecium: One pistil; about 11.5 mm long;

*Style*.—About 11 mm long and about 0.3 mm diameter; proximal color distally nearest RHS 91B with the basal 1 mm nearest RHS NN155C.

*Stigma*.—Bifid in the terminal 0.5 mm, about 0.2 mm across; color white nearest RHS NN155D.

*Ovary*.—Oblong globose; about 1 mm long and 0.5 mm across; color between RHS 150D and RHS 145D.

Androecium: Four, in two sets, two outer and two inner;

*Filaments*.—Inner set fertile, straight, to about 5.5 mm long and 0.2 mm diameter, adnate to upper lobe of corolla in basal 1.5 mm; outer set sterile, arcuate upward, to about 5 mm long and 0.3 mm diameter, arcuate in distal 2.5 mm; color both sets white, nearest RHS NN155D.

*Anther*.—Fertile on inner filaments — elliptic, versatile, longitudinal, about 1 mm long and 0.5 mm across, color nearest RHS N187C; sterile outer pair — globose, vestigial, about 0.2 mm diameter; color nearest RHS NN155D.

*Pollen*.—Abundant on fertile anthers; color nearest RHS NN155C.

Calyx: Tubular campanulate; about 5 mm long and about 2.2 mm across (without hairs) at apex;

Sepals: Five; 5 mm long with upper three lobes split in distal 0.5 mm and lower two lobes split in distal 0.2 mm; apices acute; fused in basal 4 mm; lobe apices acute; margin entire; abaxial densely pubescent and glandular with hairs about 1.0 mm long, adaxial glabrous; persistent for weeks after flower abscission and drop;

Sepal color: Variable; adaxial nearest RHS 146C, and nearest RHS N79A with undertone of nearest RHS 146A; abaxial nearest RHS 138A and between RHS 83A and N79A; abaxial hairs nearest RHS N81C;

Seed: Spatulate in outline, rounded apex and attenuate base; up to four per flower, typically one per flower; about 2 mm long and about 1 mm diameter at widest portion and about 0.5 mm thick; color nearest RHS 200A;

Winter hardiness: At least to U.S.D.A. zone 4;

Growth: Highly resistant to drought once established; grows best in full-sun;

Pest and disease resistance: Russian sage is typically resistant to deer and rodent browsing. The new plant is less prone to yellowing foliage and lower leaf drop than other known Russian sage cultivars. No other susceptibility or resistance to diseases or pests has been observed except that which is common to *Perovskia*.

It is claimed:

1. A new and distinct cultivar of hardy Russian sage plant, *Perovskia* 'Prime Time' as herein described and illustrated.

* * * * *